US00PP19345P2

(12) United States Plant Patent
Dekker

(10) Patent No.: US PP19,345 P2
(45) Date of Patent: Oct. 21, 2008

(54) ***CHRYSANTHEMUM* PLANT NAMED 'DEKLINDIPINK'**

(50) Latin Name: *Chrysanthemum×morifolium*
Varietal Denomination: Deklindipink

(75) Inventor: Cornelis W. Dekker, Hensbroek (NL)

(73) Assignee: Dekker Breeding, B.V., Hensbroek (NL)

( * ) Notice: Subject to any disclaimer, the term of this patent is extended or adjusted under 35 U.S.C. 154(b) by 0 days.

(21) Appl. No.: 11/888,423

(22) Filed: Aug. 1, 2007

(51) Int. Cl.
*A01H 5/00* (2006.01)

(52) U.S. Cl. ..... Plt./297

(58) Field of Classification Search ..... Plt./297
See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinct cultivar of *Chrysanthemum* plant named 'Deklindipink', characterized by its single-type inflorescences with obovate-shaped, light pink-colored ray florets; strong and upright flowering stems; freely flowering habit; early and uniform flowering response; plants flower about 41 days after the start of photoinductive treatments; and good postproduction longevity; plants maintain good substance for about 27 days in an interior environment.

1 Drawing Sheet

Botanical designation: *Chrysanthemum×morifolium.*
Cultivar denomination: 'DEKLINDIPINK'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Deklindipink'.

The new *Chrysanthemum* was discovered by the Inventor in a controlled greenhouse environment in Hensbroek, The Netherlands on Jan. 6, 2006, as a naturally-occurring whole plant mutation of *Chrysanthemum×morifolium* cultivar Deklindi White, disclosed in U.S. Plant Pat. No. 17,815. The new *Chrysanthemum* was observed as a single plant in a group of flowering plants of the parent cultivar. The selection of this plant was based on its ray floret coloration.

Asexual reproduction of the new *Chrysanthemum* by terminal cuttings in a controlled environment in Hensbroek, The Netherlands since Jan. 28, 2006, has shown that the unique features of this new *Chrysanthemum* are stable and reproduced true to type in successive generations.

SUMMARY OF THE INVENTION

Plants of the cultivar Deklindipink have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Deklindipink'. These characteristics in combination distinguish 'Deklindipink' as a new and distinct cultivar of *Chrysanthemum:*

1. Single-type inflorescences with obovate-shaped, light pink-colored ray florets.
2. Strong and upright flowering stems.
3. Freely flowering habit.

4. Early and uniform flowering response; plants flower about 41 days after the start of photoinductive treatments.
5. Good postproduction longevity; plants maintain good substance for about 27 days in an interior environment.

Plants of the new *Chrysanthemum* differ from plants of the parent, the cultivar Deklindi White, in the following characteristics:

1. Inflorescences of plants of the new *Chrysanthemum* have larger discs than inflorescences of plants of the cultivar Deklindi White.
2. Inflorescences of plants of the new *Chrysanthemum* have more ray florets than inflorescences of plants of the cultivar Deklindi White.
3. Plants of the new *Chrysanthemum* and the cultivar Deklindi White differ in ray floret color as plants of the cultivar Deklindi White have white-colored ray florets.
4. Plants of the new *Chrysanthemum* have longer peduncles than plants of the cultivar Deklindi White.
5. Plants of the new *Chrysanthemum* flower earlier than plants of the cultivar Deklindi White.

Plants of the new *Chrysanthemum* can be compared to plants of the *Chrysanthemum* cultivar Dekyen, not patented. In side-by-side comparisons conducted in Hensbroek, The Netherlands, plants of the new *Chrysanthemum* differed from plants of the cultivar Dekyen in the following characteristics:

1. Plants of the new *Chrysanthemum* were less vigorous than plants of the cultivar Dekyen.
2. Plants of the new *Chrysanthemum* had smaller leaves than plants of the cultivar Dekyen.
3. Plants of the new *Chrysanthemum* were more freely flowering than plants of the cultivar Dekyen.
4. Plants of the new *Chrysanthemum* had smaller inflorescences than plants of the cultivar Dekyen.

BRIEF DESCRIPTION OF THE PHOTOGRAPHS

The accompanying colored photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the top of the sheet comprises a side perspective view of a typical flowering stem of 'Deklindipink' grown as a spray type.

The photograph at the bottom of the sheet is a close-up view of typical inflorescences of 'Deklindipink'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the spring in Hensbroek, The Netherlands, under commercial practice in a glass-covered greenhouse. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels were about seven kilolux. Plants were about eight weeks from planting when the photographs and the description were taken.

Botanical classification: *Chrysanthemum×morifolium* cultivar Deklindipink.

Parentage: Naturally-occurring whole plant mutation of *Chrysanthemum×morifolium* cultivar Deklindi White, disclosed in U.S. Plant Pat. No. 17,815.

Propagation:

*Type.*—Terminal vegetative cuttings.

*Time to initiate roots.*—About six to seven days at 20° C.

*Time to produce a rooted young plant.*—About 13 to 15 days at 20° C.

*Root description/habit.*—Fine, fibrous; light brown in color; freely branching.

Plant description:

*Appearance/growth habit.*—Herbaceous single-type cut flower that is typically grown as a spray-type. Moderately vigorous growth habit.

*Flowering stem description.*—Aspect: Erect. Length: About 60 cm. Spray diameter: About 10 cm to 15 cm. Diameter: About 5 mm. Number of lateral branches: About six to eight. Internode length: About 1 cm to 2 cm. Texture: Pubescent; longitudinal ridged. Color: Close to 146B to 146C.

*Foliage description.*—Arrangement: Alternate; simple. Length: About 4 cm to 7 cm. Width: About 1.5 cm to 3.5 cm. Apex: Cuspidate. Base: Attenuate. Margin: Palmately lobed; sinuses divergent. Texture, upper and lower surfaces: Pubescent, slightly rough; veins prominent on lower surface. Color: Developing foliage, upper surface: Close to 137C. Developing foliage, lower surface: Close to 146B. Fully expanded foliage, upper surface: Close to 147A; venation, close to 146A. Fully expanded foliage, lower surface: Close to 147B; venation, 146b. Petiole: Length: About 5 mm to 15 mm. Diameter: About 1 mm to 2 mm. Texture, upper surface: Smooth. Texture, lower surface: Slightly rough. Color, upper and lower surfaces: Close to 146B.

Inflorescence description:

*Appearance.*—Single-type inflorescence form with obovate-shaped ray florets. Inflorescences borne on terminals, arising from leaf axils. Ray and disc florets develop acropetally on a capitulum. Inflorescences slightly fragrant.

*Flowering response.*—Under natural conditions, plant flower in the autumn/winter in the Northern Hemisphere. At other times of the year, inflorescence initiation and development can be induced under short day/long night conditions (at least 13.5 hours of darkness). Early and uniform flowering response; plants exposed to two weeks of long day/short night conditions after planting followed by photoinductive short day/long night conditions flower about 41 days later when grown as a spray-type.

*Postproduction longevity.*—In an interior environment, inflorescences and foliage will maintain good color and substance for about 27 days.

*Quantity of inflorescences.*—When grown as a spray type, freely flowering habit, about 8 to 13 inflorescences per flowering stem develop.

*Inflorescence size.*—Diameter: about 2 cm to 2.5 cm. Depth (height): About 1 cm. Disc diameter: About 5 mm to 6 mm. Receptacle height: About 2 mm. Receptacle diameter: About 2 mm to 3 mm. Receptacle color: Close to 145B to 145C.

*Inflorescence buds.*—Shape: Oblate. Height: About 2 mm. Diameter: About 4 mm. Color: Close to between 144A and 137C.

*Ray florets.*—Length: About 8 mm to 12 mm. Width: About 5 mm to 7 mm. Shape: Obovate. Angle: Initially upright to about 30° from vertical to eventually perpendicular to the peduncle. Apex: Rounded to tridentate. Base: Attenuate. Margin: Entire. Texture, upper and lower surfaces: Smooth, glabrous; satiny. Number of ray florets per inflorescence: About 25 to 30 arranged in about two to three whorls. Color: When opening, upper surface: Close to 75D. When opening, lower surface: Close to 75C. Fully opened, upper surface: Close to 75D; color becoming closer to 76D with development. Fully opened, lower surface: Close to 75D; towards the margin, close to 75C.

*Disc florets.*—Shape: Fused tubular, elongated. Apex: Acute. Length: About 2 mm to 4 mm. Diameter: About 0.5 mm to 1 mm. Number of disc florets per inflorescence: About 125. Color: Immature: Apex: Close to 154A. Mid-section and base: Close to 145D. Mature: Apex: Close to 2A. Mid-section and base: Close to 145D.

*Involucral bracts.*—Length: About 5 mm. Width: About 2 mm. Shape: Ovate. Apex: Rounded. Base: Rounded to truncate. Margin: Entire. Texture, upper and lower surfaces: Smooth, glabrous. Number of involucral bracts per inflorescence: About 20 arranged in about two whorls. Color, upper surface: Close to 143B. Color, lower surface: Close to 137C.

*Peduncles.*—Length, first peduncle: About 4 cm to 5 cm. Length, fourth peduncle: About 6 cm. Diameter: About 1 mm to 1.5 mm. Angle: About 30° from vertical. Strength: Moderately strong. Texture: Pubescent; longitudinally ridged. Color: Close to 146B.

*Reproductive organs.*—Androecium: Not observed. Gynoecium: Present on both ray and disc florets. Style length: About 3 mm. Style color: Close to 145D.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Deklindipink' as illustrated and described.

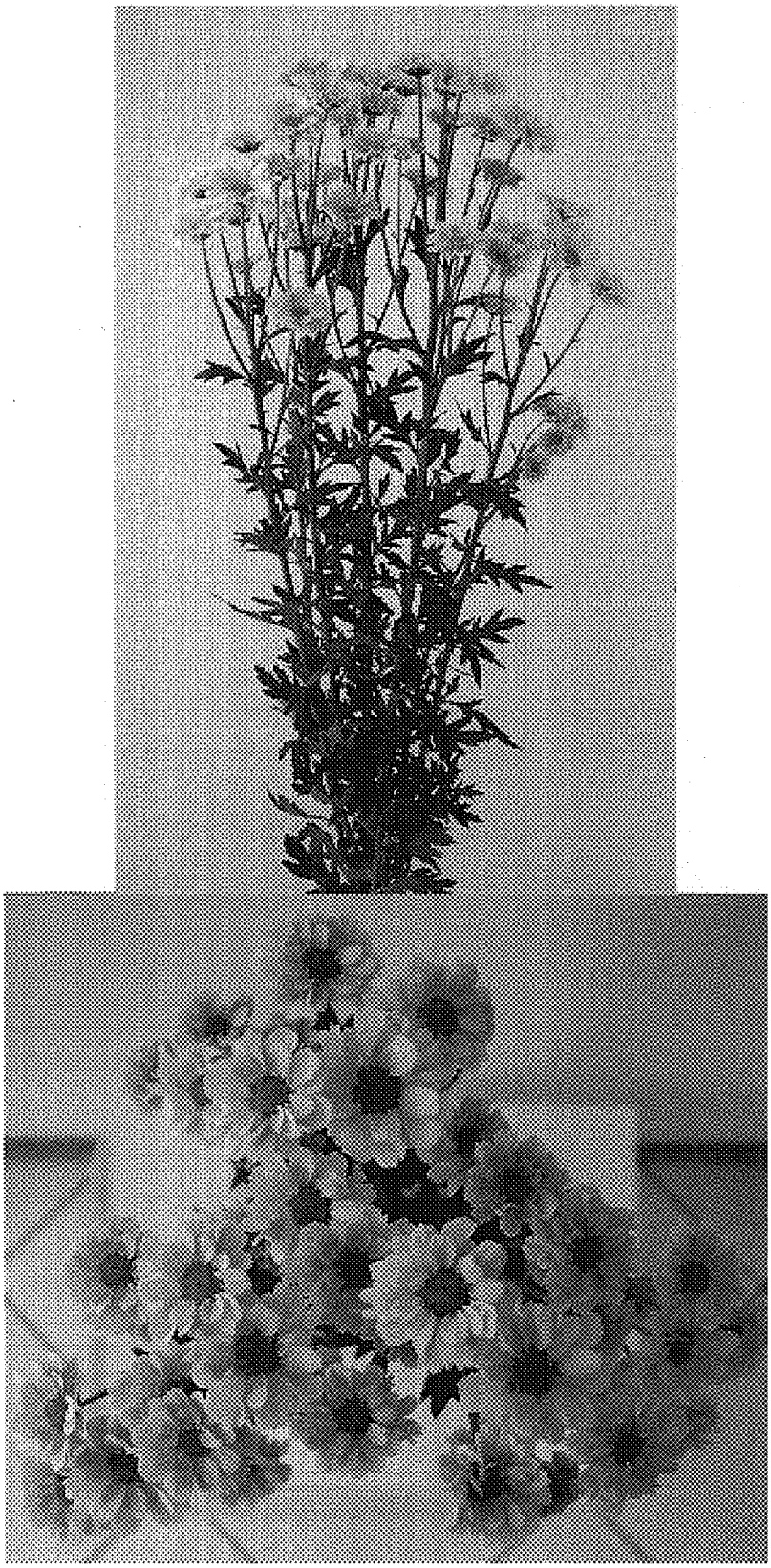

* * * * *